(12) United States Patent
St. Pierre et al.

(10) Patent No.: US 9,301,700 B2
(45) Date of Patent: Apr. 5, 2016

(54) CONFIGURABLE VITAL SIGNS SYSTEM (71) Applicant: Welch Allyn, Inc., Skaneateles Falls, NY (US)

(72) Inventors: Shawn C. St. Pierre, Skaneateles Falls, NY (US); John A. Lane, Skaneateles Falls, NY (US); David E. Quinn, Skaneateles Falls, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 674 days.

(21) Appl. No.: 13/631,046

(22) Filed: Sep. 28, 2012

(65) Prior Publication Data
US 2014/0088446 A1    Mar. 27, 2014

Related U.S. Application Data
(60) Provisional application No. 61/706,625, filed on Sep. 27, 2012.

(51) Int. Cl.
*A61B 5/02* (2006.01)
*A61B 5/022* (2006.01)
*A61B 5/00* (2006.01)

(52) U.S. Cl.
CPC ............... *A61B 5/022* (2013.01); *A61B 5/7203* (2013.01)

(58) Field of Classification Search
None
See application file for complete search history.

(56) References Cited

U.S. PATENT DOCUMENTS

| | | |
|---|---|---|
| 3,527,204 A | 9/1970 | Lem |
| 4,313,445 A | 2/1982 | Georgi |
| 4,367,751 A | 1/1983 | Link |
| 4,407,297 A | 10/1983 | Croslin |
| 4,493,326 A | 1/1985 | Hill |
| 4,617,937 A | 10/1986 | Peel |
| 4,671,290 A | 6/1987 | Miller |
| 4,729,383 A | 3/1988 | Susi |
| 4,796,184 A | 1/1989 | Bahr et al. |
| 4,889,133 A | 12/1989 | Nelson et al. |
| 4,949,710 A | 8/1990 | Dorsett et al. |
| 5,014,714 A | 5/1991 | Millay et al. |

(Continued)

FOREIGN PATENT DOCUMENTS

| | | |
|---|---|---|
| EP | 838194 A1 | 4/1998 |
| EP | 838194 B1 | 4/2003 |

(Continued)

OTHER PUBLICATIONS

Cappuccio et al., A Prospective Study of Hypertension and the Incidence of Kidney Stones in Men, Journal of Hypertension 1999, 17:1017-1022 (6 pages).

(Continued)

*Primary Examiner* — Etsub Berhanu (57) ABSTRACT

A method of determining a value indicative of a hemodynamic parameter of a patient includes performing a plurality of value determinations. Performing the plurality of value determinations includes determining a first value indicative of the hemodynamic parameter, determining, with a controller, a difference between the first value and a baseline associated with the first value, and replacing the baseline with the first value, in a memory of the controller, if the difference is outside of a predetermined range. The method also includes determining an estimate of the hemodynamic parameter based on acceptable values determined during the plurality of value determinations.

29 Claims, 4 Drawing Sheets

(56) References Cited

U.S. PATENT DOCUMENTS

| | | | |
|---|---|---|---|
| 5,025,791 A | 6/1991 | Niwa | |
| 5,170,795 A | 12/1992 | Ramsey, III | |
| 5,253,648 A | 10/1993 | Walloch | |
| 5,267,567 A | 12/1993 | Aung | |
| 5,339,818 A | 8/1994 | Baker et al. | |
| 5,348,004 A | 9/1994 | Hollub | |
| 5,349,519 A | 9/1994 | Kaestle | |
| 5,392,781 A | 2/1995 | Phillipps et al. | |
| 5,404,878 A | 4/1995 | Frankenreiter et al. | |
| 5,485,848 A | 1/1996 | Jackson | |
| 5,577,508 A | 11/1996 | Medero | |
| 5,606,977 A | 3/1997 | Ramsey et al. | |
| 5,649,536 A | 7/1997 | Ogura | |
| 5,651,370 A | 7/1997 | Hersh et al. | |
| 5,752,913 A | 5/1998 | Oka et al. | |
| 5,752,919 A | 5/1998 | Schrimpf | |
| 5,758,652 A | 6/1998 | Nikolic | |
| 5,772,601 A | 6/1998 | Oka et al. | |
| 5,791,348 A | 8/1998 | Aung | |
| 5,836,887 A | 11/1998 | Oka et al. | |
| 5,971,932 A | 10/1999 | Okamoto | |
| 6,083,172 A | 7/2000 | Baker et al. | |
| 6,099,476 A | 8/2000 | Engel et al. | |
| 6,168,567 B1 | 1/2001 | Pickering et al. | |
| 6,196,974 B1 | 3/2001 | Miwa et al. | |
| 6,236,872 B1 | 5/2001 | Diab | |
| 6,322,516 B1 | 11/2001 | Inukai et al. | |
| 6,322,517 B1 | 11/2001 | Yamamoto et al. | |
| 6,324,421 B1* | 11/2001 | Stadler et al. | 600/509 |
| 6,405,076 B1 | 6/2002 | Taylor | |
| 6,428,481 B1 | 8/2002 | Inukai et al. | |
| 6,443,905 B1 | 9/2002 | Nissila | |
| 6,500,127 B1 | 12/2002 | Inukai et al. | |
| 6,503,206 B1 | 1/2003 | Li et al. | |
| 6,602,199 B2 | 8/2003 | Chen et al. | |
| 6,656,116 B2 | 12/2003 | Kim et al. | |
| 7,515,961 B2 | 4/2009 | Germanson et al. | |
| 7,678,060 B1 | 3/2010 | Millen | |
| 8,016,765 B2 | 9/2011 | Ramsey | |
| 8,114,026 B2 | 2/2012 | Leschinsky | |
| 8,197,416 B1 | 6/2012 | Shankar | |
| 2002/0035332 A1* | 3/2002 | Chen et al. | 600/490 |
| 2004/0019284 A1 | 1/2004 | Kawaguchi et al. | |
| 2004/0167411 A1 | 8/2004 | Kolluri et al. | |
| 2007/0038129 A1 | 2/2007 | Kishimoto et al. | |
| 2007/0118036 A1 | 5/2007 | Hersh et al. | |
| 2008/0146891 A1* | 6/2008 | Wang et al. | 600/300 |
| 2009/0062664 A1 | 3/2009 | Chang et al. | |
| 2009/0143694 A1* | 6/2009 | Krauss et al. | 600/532 |
| 2009/0312652 A1 | 12/2009 | Yamakoshi et al. | |
| 2010/0016684 A1* | 1/2010 | Czer | 600/301 |
| 2010/0234742 A1 | 9/2010 | Lin et al. | |
| 2010/0331724 A1 | 12/2010 | Watson et al. | |
| 2011/0028854 A1* | 2/2011 | Addison et al. | 600/493 |
| 2011/0066006 A1 | 3/2011 | Banet et al. | |
| 2011/0077535 A1 | 3/2011 | Chen et al. | |
| 2011/0082357 A1* | 4/2011 | Hornick | 600/364 |
| 2011/0092830 A1 | 4/2011 | Chen et al. | |
| 2011/0118618 A1* | 5/2011 | John et al. | 600/544 |
| 2011/0160597 A1 | 6/2011 | Lane et al. | |
| 2011/0218447 A1 | 9/2011 | Kinoshita | |
| 2012/0220884 A1 | 8/2012 | Yamashita et al. | |
| 2012/0226173 A1 | 9/2012 | Quinn et al. | |

FOREIGN PATENT DOCUMENTS

| | | |
|---|---|---|
| JP | 06133938 A | 5/1994 |
| JP | 10066679 A | 3/1998 |
| JP | 10137202 A | 5/1998 |
| JP | 10151118 A | 6/1998 |
| JP | 2002191568 A | 7/2002 |
| WO | 8603114 A1 | 6/1986 |
| WO | 0150952 A1 | 7/2001 |
| WO | 2005020808 A1 | 3/2005 |
| WO | 2007025341 A1 | 3/2007 |
| WO | 2011110491 A1 | 9/2011 |

OTHER PUBLICATIONS

O'Brien et al., The British Hypertension Society Protocol for the Evaluation of Blood Pressure Measuring Devices, Journal of Hypertension 1993, 11 (suppl 2):543-562 (20 pages).

Goonasekera et al., Random Zero Sphygmomanometer Versus Automatic Oscillometric Blood Pressure Monitor; is Either the Instrument of Choice?, Journal of Human Hypertension (1995) 9, 885-889 (5 pages).

International Search Report/Written Opinion for PCT/US2013/060307, Dated Jan. 6, 2014 (12 pages).

Semi-automatic digital blood pressure arm monitor, adult Source: http://www.shop.gorillascientific.com/Semi-Automatic-Digital-Blood-Pressure-Arm-Monitor-Adult-01-5041.htm?gclid=CIWD57_WkrlCFWXhQgod4FIAfg Date Accessed: Sep. 10, 2012.

Elemano digital automatic hybrid blood pressure monitor Source: http://www.ebay.com/itm/ELEMANO-DIGITAL-AUTOMATIC-HYBRID-BLOOD-PRESSURE-MONITOR-/270631061733#vi-content Date Accessed: Sep. 10, 2012.

Taking an Automated and Manual Blood Pressure Reading with the SunTech 247 Source: http://www.suntechmed.com/support/customer-technical-supoort/video-tutorials/207-taking-an-automated-and-manual-blood-pressure-reading-with-the-suntech-247 Date Accessed: Sep. 10, 2012.

Appel et al., Ambulatory Blood Pressure Monitoring and Blood Pressure Self-Measurement in the Diagnosis and Management of Hypertension, Annals of Internal Medicine, Jun. 1, 1993 vol. 118 No. 11, 867-882.

Owens et al., Diagnosis of White Coat Hypertension by Ambulatory Blood Pressure Monitoring, Scientific Contributions, Hypertension, 1999; 34:267-272 (7 pages).

Michell, Routine Blood Pressure Measurement: application of the standard canine technique in a human, University of London (Royal Veterinary College), Aug. 1996;1(4):385-387.

Kuulasmaa et al., Quality Assessment of Data on Blood Pressure in the WHO MONICA Project, May 1998, http://www.thi.fi/publications/monica/bp/bpga.htm, Date Accessed: Jul. 12, 2012.

\* cited by examiner

FIG. 1

```
DELAY      [90]  sec    [SAVE]  VALUE  [SYSTOLIC ]
INTERVAL   [10]  sec                   [DIASTOLIC]
BASELINE   [120] mmHg   [SYSTOLIC]     [D̶I̶A̶S̶T̶O̶L̶I̶C̶]
RANGE    + [10]  mmHg - [10] mmHg

NUMBER OF VALUE DETERMINATIONS          [6]
OMIT VALUE(S)?  [Y]  [N]

• SELECT VALUE DETERMINATION
         FOR OMISSION  ①②③④⑤⑥
PROGRAM: AVERAGE PATIENT
```

FIG. 2

```
SELECT PROGRAM              [START]

[√]    AVERAGE PATIENT

[ ]    HIGH BP PATIENT_GERIAT

[ ]    HIGH BP PATIENT_MID

[ ]    HIGH BP PATIENT_BARIAT

[ ]    LOW BP PATIENT
```

FIG. 3

AVERAGE PATIENT  RANGE: ±10 mmHg

VALUE:  BASELINE: 120 mmHg

1) ~~140/80~~   t
2) ~~125/80~~   140
3) ~~114/82~~   125
4) ~~103/69~~   114
5) 101/70       103      ESTIMATE
6) 102/71       103      101.5/70.5 mmHg

FIG. 4

AVERAGE PATIENT  RANGE: ±10 mmHg

VALUE:  BASELINE: 120 mmHg

1) ~~140/80~~   120
2) ~~125/80~~   140
3) ~~114/82~~   125
4) ~~103/69~~   114
5) ~~115/75~~   103      ESTIMATE
6) ~~127/79~~   115       -

CONFIGURABLE VITAL SIGNS SYSTEM

CROSS-REFERENCE TO RELATED APPLICATION

This application claims the benefit of U.S. Provisional Application No. 61/706,625, filed Sep. 27, 2012, the entire disclosure of which is incorporated herein by reference.

TECHNICAL FIELD

This application is directed to systems and methods for monitoring a patient, and in particular, to systems and methods for determining an estimate of a hemodynamic parameter of the patient.

BACKGROUND

Traditional non-invasive blood pressure monitoring devices operate by inflating a cuff to a pressure well above a patient's systolic blood pressure. Because the systolic pressure is usually not known prior to inflation, the cuff must be inflated to such a high pressure to ensure that the patient's arterial blood flow is completely occluded. Once well above systole, the cuff is deflated and the systolic and diastolic pressures are calculated based on signals provided during cuff deflation.

Some systems and methods have been developed to determine blood pressures during cuff inflation. These methods, however, are generally inaccurate and/or slow. Consequently, such methods cannot provide a commercially useful determination of systolic pressure that must meet certain regulatory standards.

Other systems and method have been developed to automatically take a sequence of systolic and diastolic blood pressure measurements, and to estimate blood pressure based on an average of the measured systolic and diastolic blood pressures.

For example, U.S. Pat. No. 6,602,199 ("the '199 patent") teaches a system configured to take a predetermined number of consecutive systolic and diastolic blood pressure measurements of a patient. The system of the '199 patent includes a blood pressure cuff, a sensor, and a control module configured to determine an estimated blood pressure of the patient based on the sequence of measurements.

While the system of the '199 patent may provide a rough estimate of patient blood pressure, such systems are typically characterized by several significant drawbacks when used in patient monitoring environments. For example, such systems typically take measurements over a span of several minutes before determining the estimated blood pressure value. In hospitals, physicians' offices, clinics, and other like healthcare facilities, however, such a long lead time prior to determining the blood pressure measurement may result in extended patient wait times and an overall decrease in facility efficiency. In addition, such systems are generally not configured to adapt to variations in patient blood pressure occurring throughout the sequence of measurements. As a result, the blood pressure estimate provided by such systems may be inaccurate.

The various exemplary embodiments of the present disclosure are directed toward overcoming one or more of the deficiencies of the prior art.

SUMMARY

In a first exemplary embodiment of the present disclosure, a method of determining a value indicative of a hemodynamic parameter of a patient includes performing a plurality of value determinations. Performing the plurality of value determinations includes determining a first value indicative of the hemodynamic parameter, determining, with a controller, a difference between the first value and a baseline associated with the first value, and replacing the baseline with the first value, in a memory of the controller, if the difference is outside of a predetermined range. The method also includes determining an estimate of the hemodynamic parameter based on acceptable values determined during the plurality of value determinations.

In another exemplary embodiment of the present disclosure, a method of determining a value indicative of a blood pressure of a patient includes automatically performing a plurality of value determinations, in a closed-loop manner, in response to receiving at least one input associated with the plurality of values. Performing the plurality of value determinations includes inflating a cuff disposed around a limb of the patient until a vessel within the limb is at least partially occluded, determining a first blood pressure value of the patient while the cuff is being inflated, and determining whether a component of the first blood pressure is within a predetermined range of a baseline blood pressure value. Performing the plurality of value determinations also includes substantially deflating the cuff and reinflating the cuff until the vessel is at least partially occluded, determining a second blood pressure value of the patient while the cuff is being reinflated. Performing the plurality of value determinations further includes determining, if the first blood pressure value is within the predetermined range of the baseline, whether the second blood pressure value is within the predetermined range of the baseline, or if the first blood pressure is outside of the predetermined range of the baseline, whether the second blood pressure is within the predetermined range of the first blood pressure value. The method also includes determining an estimate of the blood pressure of the patient, wherein the estimate is based on at least one of the first and second blood pressure values.

In a further exemplary embodiment of the present disclosure, a patient monitoring system includes a sensor configured to determine a value indicative of a hemodynamic parameter of the patient during transition of a vessel of the patient from unoccluded to at least partially occluded, and a controller in communication with the sensor. The controller includes a memory and is configured to assist in performing a plurality of value determinations. In such an exemplary embodiment, performing the plurality of value determinations includes determining a first value indicative of the hemodynamic parameter, determining a difference between the first value and a baseline associated with the first value, and replacing the baseline with the first value, in the memory of the controller, if the difference is outside of a predetermined range. The controller is further configured to determine an estimate of the hemodynamic parameter based on acceptable values determined during the plurality of value determinations.

DETAILED DESCRIPTION

Figure 1:
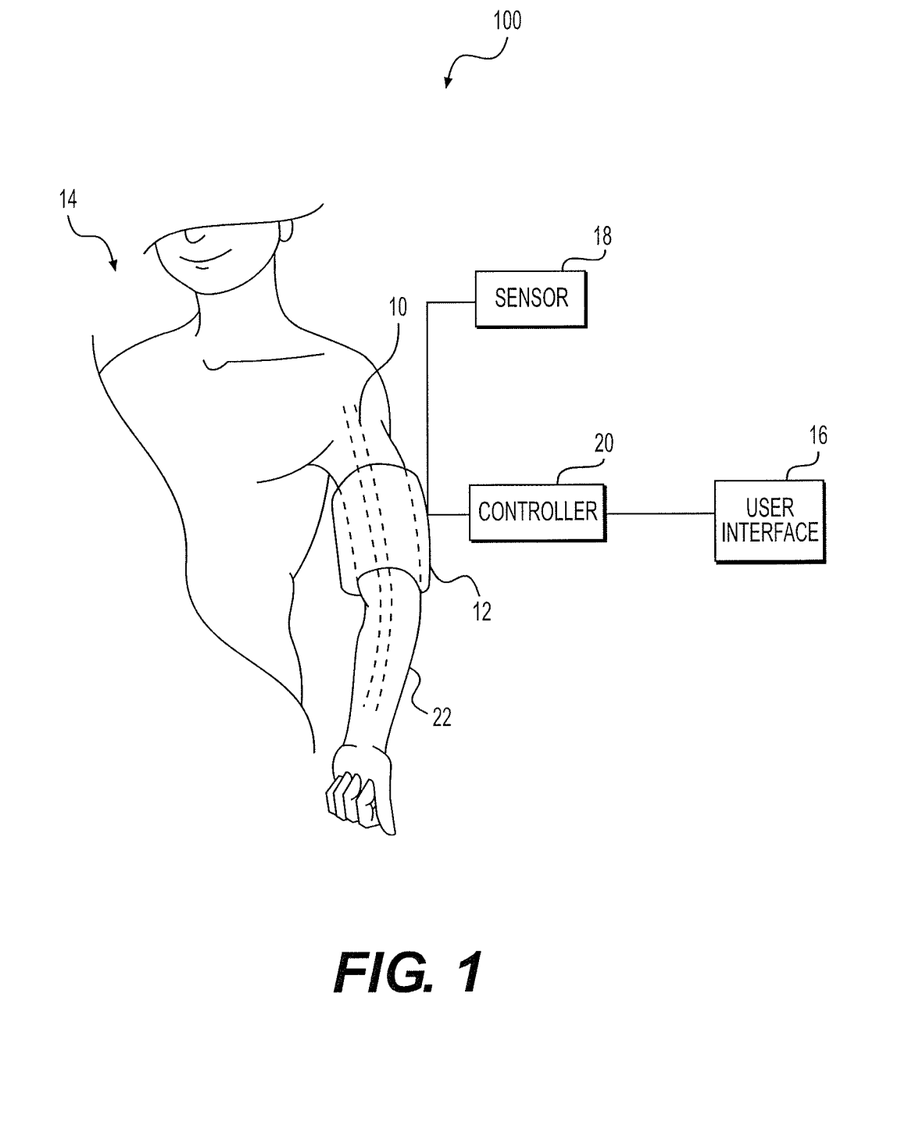
FIG. 1 illustrates a patient monitoring system according to an exemplary embodiment of the present disclosure.

FIG. 1 illustrates a patient monitoring system 100, according to an exemplary embodiment of the present disclosure. System 100 can be configured to monitor a patient, and in some embodiments, to determine a hemodynamic parameter of the patient. As used herein, the term "hemodynamic parameter" can include an indication of cardiac or vascular health, such as, for example, an indication of cardiac, circulatory, or vascular functionality. Specifically, a hemodynamic parameter can include a heart rate, a blood pressure, a vessel compliance, an aortic index, an augmentation index, reflected wave ratio, or an indication of treatment. Blood pressure can include systolic, diastolic, or mean atrial pressure. It is understood that such blood pressures may be represented as a systolic blood pressure over a diastolic blood pressure, and that a mean or average blood pressure may be represented as an average systolic blood pressure over an average diastolic blood pressure. Moreover, an indication of treatment can include a parameter reflecting the affect of a drug treatment, or one or more treatments of a disease state.

System 100 can include a cuff 12 configured to at least to partially occlude the movement of blood through a vessel 10 of patient 14 such as an artery, vein, or the like. In some embodiments, cuff 12 can be configured to completely occlude an artery of patient 14. Although shown in FIG. 1 surrounding the arm 22 of patient 14, cuff 12 may be adapted for placement on any suitable part of patient 14, including, for example, a wrist, a finger, an upper thigh, or an ankle. In addition, one or more cuffs 12 could be placed at different locations about patient 14 for use with system 100.

Cuff 12 can include an inflatable device, wherein the pressure or volume within cuff 12 may be controlled by any known inflation device (not shown) operably associated with cuff 12. Such inflation devices can include a pump or similar device configured to controllably inflate and/or deflate cuff 12. For example, such inflation devices could supply cuff 12 with a fluid to increase the pressure or volume of cuff 12. In other embodiments, one or more inflation devices could include mechanical, electrical, or chemical devices configured to control vessel occlusion of patient 14 via cuff 12. In some embodiments, such inflation devices can generally maintain cuff 12 at about a target pressure.

System 100 can further include a sensor 18 configured to receive a signal associated with patient 14. In some embodiments, sensor 18 can be configured to receive a signal associated with an at least partially occluded vessel 10 of patient 14. Such an input signal can arise from blood movement through a partially occluded vessel 10 or from a signal associated with an occluded blood vessel 10. Sensor 18 could sample multiple times at various intervals. In yet other embodiments, sensor 18 could provide an indication of blood vessel movement, such as, for example, oscillations arising from vascular expansion or contraction. For example, sensor 18 could be configured to detect a pressure or volume of cuff 12 that may vary periodically with the cyclic expansion and contraction of an artery of patient 14. In particular, sensor 18 could determine a blood pressure or other hemodynamic parameter associated with patient 14 using an oscillometric method.

In some embodiments, sensor 18 could detect a volume or a pressure associated with cuff 12. For example, sensor 18 could include a pressure sensor and may be located within or about cuff 12. System 100 could further operate with a plurality of sensors 18, and may include a high-resolution sensor or pneumatic sensor designed to operate in conjunction with cuff 12.

Sensor 18 can further be configured to generate an output signal. The output signal may be generated based on an input signal received from patient 14. In one aspect, the output signal can include a representation of an input signal associated with cuff 12 and/or patient 14.

Cuff 12, the cuff inflation devices described above, and sensor 18 may be operably associated with a controller 20. Specifically, controller 20 could include one or more processors configured to control one or more operations of cuff 12, cuff inflation devices, or sensor 18. For example, controller 20 can control inflation of cuff 12 via control of the inflation devices described above.

In some embodiments, controller 20 can calculate a target pressure. This calculation may be based on an output signal from sensor 18, as described above. Controller 20 may also control inflation of cuff 12, inflation of cuff 12 to the target pressure, or generally maintaining inflation of cuff 12 at about the target pressure.

In some embodiments, a hemodynamic parameter can be determined based on a suprasystolic measurement. In other embodiments, a hemodynamic parameter can be determined based on a first set of data obtained during inflation of cuff 12 and a second set of data obtained during general maintenance of cuff 12 at about the target pressure mentioned above. The first or second sets of data can include various data associated with a signal waveform associated with patient 14 and/or cuff 12, and may include amplitude, frequency, morphology, feature, or mathematically derived data. Data can be derived from a derivative, integration, or frequency analysis, such as, for example, a fast-Fourier transform. Data may also be derived from various algorithms, including curve fitting, neural network, filtering, smoothing, or data processing.

Although not shown in FIG. 1, in additional exemplary embodiments, system 100 can optionally include a signal analysis module and/or an accelerometer. These components may operate with one or more of the components of system 100 as described above. For example, the signal analysis module may be configured to analyze one or more signals using one or more processors. Such analysis may be based on the output signal of sensor 18. For example, the signal analysis module can include one or more filters configured to filter a signal associated with sensor 18 or controller 20. Such filters can include band-pass, high-pass, or low-pass filters.

In exemplary embodiments, the accelerometer described above may be configured to detect movement of limb 22 and/or of patient 14. The accelerometer can be configured to detect movement in one, two, or three dimensions. A signal arising from the accelerometer could be used to provide additional information to another component of system 100. For example, if movement of patient 14 is sufficient to interfere with sensor 18, a signal from the accelerometer may be transmitted to controller 20 to halt one or more measurements. In addition, a signal from the accelerometer may be transmitted to the signal analysis module described above to cancel or reset a calculation. Data obtained from sensor 18 could be combined with data from the accelerometer to determine if an irregular signal may be caused by a motion artifact. Various data from the accelerometer may be processed to provide additional data to determine one or more hemodynamic parameters.

System 100 can further include a user interface 16 configured to provide communication to patient 14 or one or more operators. For example, user interface 16 could include a display configured to display one or more hemodynamic parameters. As will be described in greater detail below, FIGS. 2-5 illustrate exemplary displays associated with user interface 16. In other embodiments, user interface 16 could include a transmitter configured to transmit data to a remote location. User interface 16 may further include audio output to communicate with patient 14 and/or an operator of system 100.

In addition to the components outlined above, system 100 may include various other components as required, such as, for example, a memory, a power source, and a user input. One or more components described herein may be combined or may be separate and operate with wireless or wired communication links. Moreover, the various components of system 100 could be integrated into a single processing unit or may operate as separate processors. In operation, one or more processors can be configured to operate in conjunction with one or more software programs to provide the functionality of system 100. For example, one or more of the components described above with respect to system 100 may include one or more hardware components and/or one or more software components configured to control operation of such components and/or of system 100.

Figure 6:
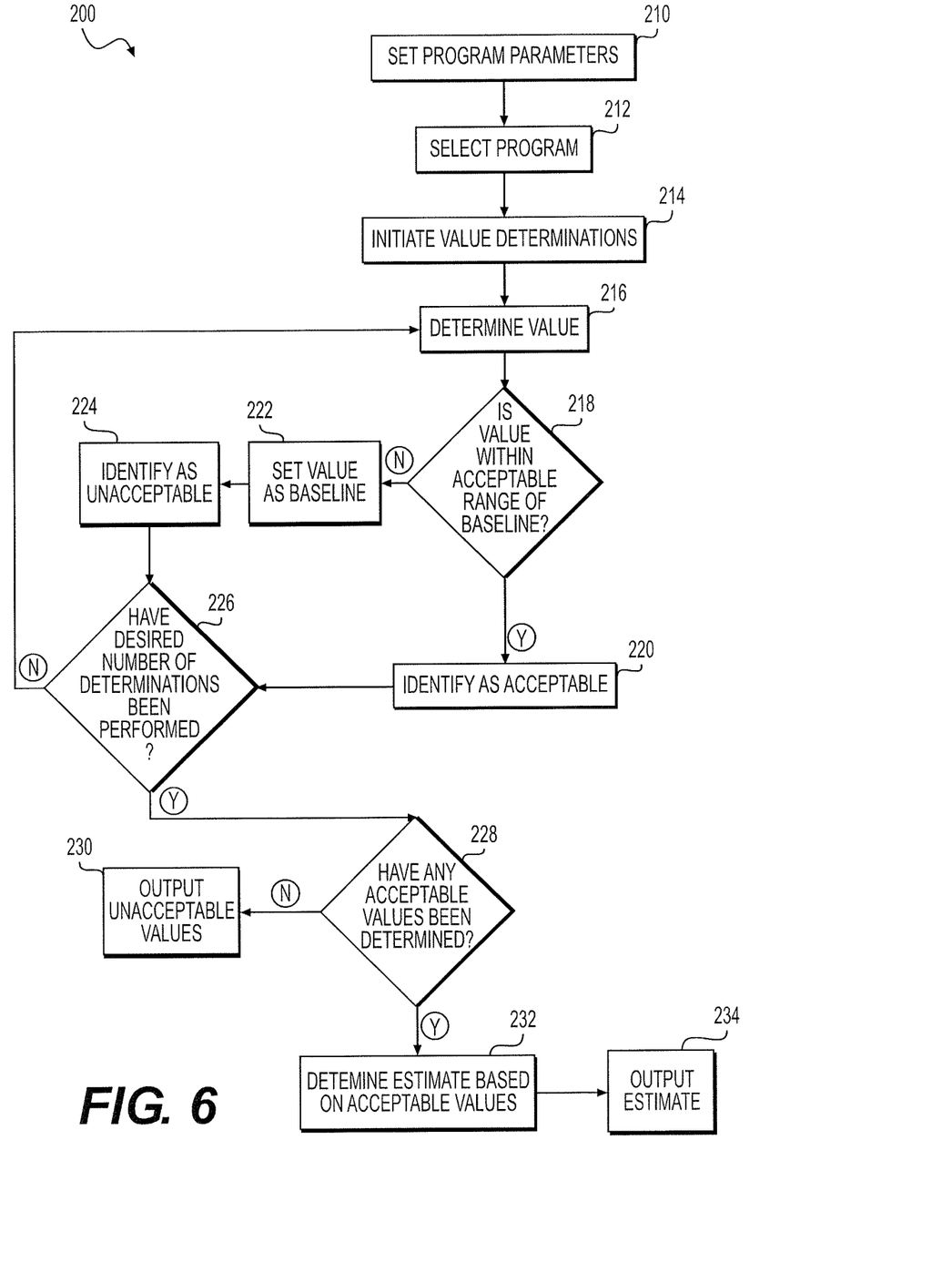
FIG. 6 illustrates a flow chart according to an exemplary embodiment of the present disclosure.

FIG. 6 illustrates a flow chart 200 according to an exemplary embodiment of the present disclosure. Each step described below with respect to FIG. 6 can be understood as corresponding to one or more computational instructions. These computational instructions can operate based on hardware and/or software components of system 100, and may operate on one or more processors of controller 20.

In an exemplary embodiment, the method illustrated by flow chart 200 may include one of more steps required to position, activate and/or calibrate the various components of system 100. For example, system 100 may be turned on, a calibration protocol may be started, cuff 12 may be placed around patient's limb 22, an operator may enter information to identify a particular patient 14, or information could be extracted from a database. Further, various components of system 100 may be calibrated or tested to ensure proper functioning. These operations could include a check of cuff integrity, if sufficient power is available, a calibration of one or more sensors 18, or confirmation of proper processor functioning. Also, other information may be entered into system 100, such as a patient identification, weight, gender, height, or other suitable data.

Figure 3:
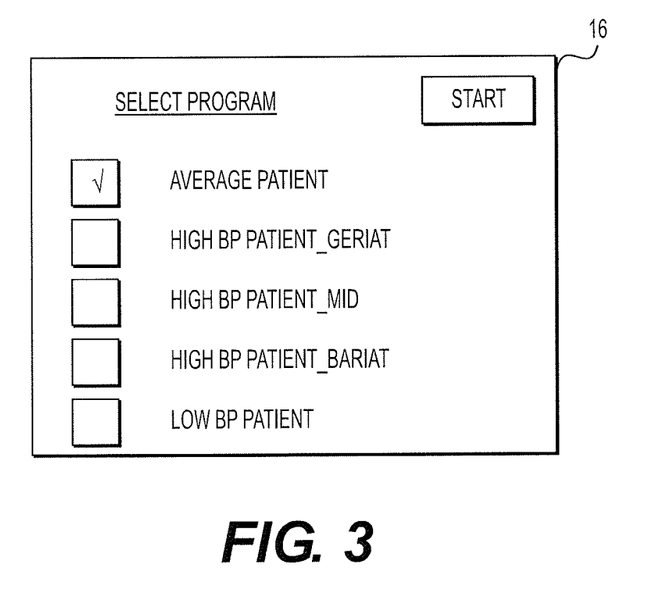
FIG. 3 illustrates another user interface associated with the exemplary patient monitoring system of FIG. 1.

At Step: 210, the user may create one or more programs associated with a sequence of value determinations and may set one or more program parameters associated with the sequence. In particular, at Step: 210, the system 100 may provide the user with the option of creating and saving one or more such programs for future use, and such exemplary programs are illustrated by the display of the exemplary user interface 16 shown in FIG. 3. In exemplary embodiments, a user may create and/or save programs tailored to the specialized needs of different patients or groups of patients. As shown in FIG. 3, such groups of patients may include, but are not limited to, for example, patients known to have a blood pressure or other hemodynamic parameter approximating an average blood pressure for a majority of the user's patients, patients known to have high blood pressure, and/or patients known to have low blood pressure. As shown in FIG. 3, such groups of patients may be characterized and/or otherwise further distinguished based on one or more physical characteristics (e.g., height, weight, gender, sex, age, etc.) of the patient, and the programs created by the user at Step 210 may be tailored to such characteristics if desired.

Figure 2:
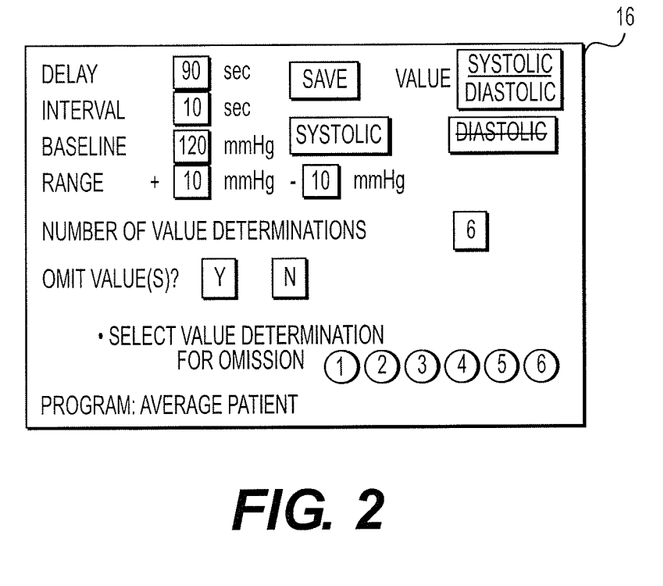
FIG. 2 illustrates a user interface associated with the exemplary patient monitoring system of FIG. 1.

FIG. 2 illustrates a display of an exemplary user interface 16 corresponding to Step: 210. As shown in FIG. 2, setting one or more program parameters associated with a sequence of value determinations may include user selection of a plurality of measurement parameters. For example, at Step: 210, the user may provide one or more inputs to controller 20 via user interface 16. Such inputs may include and/or may otherwise be indicative of, for example, one or more of a delay or wait time associated with initiating the sequence of value determinations, a time interval between initiation of each consecutive value determination made during the sequence, a baseline value associated with the sequence of value determinations, and a selection of the value to be determined during the sequence of value determinations. In such embodiments, an exemplary baseline value may include, for example, an initial systolic blood pressure value, an initial diastolic blood pressure value, an initial average blood pressure value represented as an average systolic blood pressure value over an average diastolic blood pressure value, an initial heart rate, an initial $SpO_2$ value, and/or any other like value with which one or more values determined during the sequence of value determinations may be compared. In further exemplary embodiments, the baseline value may not be selected by the user as an input. Instead, an initial value determined at Step: 216 (discussed in greater detail below) may be utilized as the baseline, and one or more additional values determined during the sequence of value determinations may be compared against such an initial determined value. In such exemplary embodiments, the selected baseline described above may not be output by the exemplary display associated with the user interface 16 illustrated in FIG. 2. Additionally, it is understood that the value to be determined may include systolic blood pressure, diastolic blood pressure, systolic blood pressure over diastolic blood pressure, heart rate, $SpO_2$, temperature, and/or any other like value indicative of a hemodynamic parameter of the patient. Such values may be selected via user interface 16 during Step: 210 in any number of ways including, for example, selecting from a drop-down menu or directly typing the value selection.

As shown by FIG. 2, inputs provided by the user at Step: 210 may also include and/or may otherwise be indicative of, for example, one or more of a range associated with the value and/or values selected by the user, and a number of value determinations to be performed during the sequence. In such embodiments, the selected range associated with the value may be, for example, a set of one or more boundary conditions, and as will be discussed in greater detail below, such a range may be used in characterizing and/or otherwise identifying individual values determined during the value determination sequence as being either "acceptable" or "unacceptable." As shown in FIG. 2, in exemplary embodiments in which the value selected by the user comprises a systolic blood pressure of the patient over a diastolic blood pressure of the patient, and the selected baseline value comprises a systolic blood pressure of 120 mmHg, the selected range may comprise a value (i.e., plus or minus) associated with the baseline, the selected value, and/or a component thereof. For example, in the embodiment shown in FIG. 2, a measured systolic blood pressure value that is within a selected range of 10 mmHg (plus or minus) of the baseline of 120 mmHg may be identified as being "acceptable" for blood pressure estimate determinations. To the contrary, in such embodiments, a measured systolic blood pressure value that is outside of the selected range of 10 mmHg (plus or minus) of the baseline of 120 mmHg may be identified as "unacceptable" for blood pressure estimate determinations. In such exemplary embodiments, a difference between the measured value and the baseline may be compared to the selected range, and if such a difference is within the selected range, the measured value may be identified as "acceptable" for blood pressure estimate determinations. Likewise, if such a difference is outside of the selected range, the measured value may be identified as "unacceptable."

With continued reference to FIG. 2, inputs provided by the user at Step: 210 may also include and/or may otherwise be indicative of, for example, one or more of an instruction whether or not to omit a value determined during one or more of the value determinations of the sequence. In exemplary embodiments in which the user provides an input comprising an instruction to omit such a value, the user may also select which of the value determinations should be omitted during determination of, for example, an average blood pressure and/or other hemodynamic parameter of the patient. As shown in FIG. 2, in exemplary embodiments, a display of user interface 16 may provide a numbered list corresponding to the number of value determinations selected by the user, and the user may select, via user interface 16, one or more of the value determinations for omission. In exemplary embodiments, the user may make such a selection and/or otherwise provide such an input prior to performance of the sequence of value determinations, during performance of the sequence of value determinations, or after performance of the sequence. As is also illustrated in FIG. 2, in exemplary embodiments, a display of user interface 16 may also output the name and/or other information associated with the program being set at Step: 210, and in further exemplary embodiments, user interface 16 may provide the user with the option of saving the information, parameters, selections, and/or other inputs provided at Step: 210.

In still further exemplary embodiments, inputs provided by the user at Step: 210 may also include and/or may otherwise be indicative of, for example, one or more of an acceptable value trending range, an acceptable envelope and/or curve profile, an acceptable signal quality range, and/or any other acceptability criterion related to the determination of blood pressure, heart rate, $SpO_2$, temperature, and/or other hemodynamic parameters. For example, at Step: 210, the user may provide an input indicative of an acceptable rate of change associated with the value being determined. In such embodiments, exemplary methods of the present disclosure may include a comparison of an actual rate of change of the determined value with a minimum and/or maximum rate of change input by the user. Such a comparison may be utilized by controller 20 to determine whether the values determined during the sequence of value determinations are trending up at an acceptable/unacceptable rate, trending down at an acceptable/unacceptable rate, or staying relatively constant. In some situations, it may be preferable to determine such values while such values remain at substantially steady state.

In exemplary embodiments in which the user provides, at Step: 210, an input indicative of an acceptable envelope and/or profile, such inputs may be associated with typical blood pressure, heart rate, $SpO_2$, temperature, and/or other hemodynamic parameter envelopes known in the art. For example, the user may provide an input indicative of an acceptable blood pressure envelope, and such an acceptable envelope may be associated with a desired profile and/or area under the curve related to a plot of blood pressure versus time. Such a plot may be output by an exemplary display of user interface 16 during performance of the exemplary methods described herein. In exemplary embodiments, an actual blood pressure envelope associated with patient 14 may be compared to a desired blood pressure envelope input by the user. For example, such a desired blood pressure envelope may be indicative of historical data, known acceptable blood pressure data, and/or average patient blood pressure data. Controller 20 may determine a difference between the desired blood pressure envelope and the actual envelope, and such a difference may be used to determine, for example, the acceptability of the determined values described above. For example, a relatively large difference between the actual and desired blood pressure envelopes may be indicative of one or more unacceptable values.

Additionally, in exemplary embodiments in which the user provides, at Step: 210, an input indicative of an acceptable signal quality, such inputs may be associated with the strength, quality, and/or integrity of signals received by the one or more sensors 18 while determining blood pressure, heart rate, $SpO_2$, temperature, and/or other values described herein. The quality of such signals may vary based on, among other things, patient movement, sensor positioning, and/or other factors known in the art. In such embodiments, the user may provide an input indicative of an acceptable range of signal quality, and the input may be used by controller 20 to determine which, if any, signals should be utilized to determine the estimate of the hemodynamic parameter. For example, patient movement during the determination of blood pressure and/or other values may create related movement artifacts and/or other noise in the sensor signal transmitted to controller 20. In other examples, wax build-ups or other blockages may create related temperature determination artifacts and/or other noise in temperature sensor signals transmitted to controller 20. If levels of such noise exceeds a predetermined noise threshold, the corresponding values may be automatically omitted from the determination of the hemodynamic parameter estimate.

Moreover, it is understood that the above description of the various user inputs received at Step: 210 is merely exemplary. At least one of the inputs described herein may, instead, comprise an output of system 100. For example, controller 20 may output indicia indicative of, for example, one or more of an acceptable value trending range, an acceptable envelope and/or curve profile, an acceptable signal quality range, and/or any other acceptability criterion related to the hemodynamic parameters described herein. Such indicia may be automatically determined by controller 20 using one or more indicia algorithms. Such indicia may be output via user interface 16 and/or may otherwise be used by controller 20 to filter and/or process the values determined during the sequence of value determinations.

At Step: 212, the user may select a desired program from a list of programs stored in a memory of controller 20. As described above, a list of several such exemplary programs is illustrated by the display of the exemplary user interface 16 shown in FIG. 3. It is understood that such a selection may be made at Step: 212 via user interface 16 in any known manner, and if only a single program is stored in memory of controller 20, the list of exemplary programs may only include the single stored program. As described above, selection of such a program at Step: 212 may be made by the user based on one or more physical characteristics (e.g., height, weight, gender, sex, age, etc.) particular to the patient being monitored.

Once the parameters have been set and the desired program has been selected, the user may provide an input requesting initiation of the value determination sequence via, for example, a "start" button or other like component of user interface 16. Such an exemplary component is illustrated in FIG. 3. At Step: 214, controller 20 may initiate a sequence comprising a plurality of value determinations in response to the user's request. Initiation of the sequence of value determinations at Step: 214 may include, for example, commencing inflation of cuff 12 previously positioned around limb 22 of patient 14. In order to commence inflation, controller 20 may, for example, operate one or more of the inflation, deflation, and/or control components discussed above so as to at least partially occlude vessel 10. It is understood that initiation at Step: 214 may also include, for example, configuring, calibrating, and/or activating one or more sensors 18.

Control may then proceed to Step: 216 where controller 20, one or more sensors 18, and/or other components of system 100 may measure, calculate, sense, estimate, and/or otherwise determine a value indicative of a hemodynamic parameter of patient 14. For example, sensor 18 may determine a systolic blood pressure, a diastolic blood pressure, a $SpO_2$ value, and/or any of the other values described herein. In further exemplary embodiments in which system 100 includes more than one sensor 18 in communication with controller 20, Step: 216 may include determining a first value indicative of a first hemodynamic parameter of patient 14 using a first sensor 18, and determining a second value indicative of a second hemodynamic parameter of patient 14 using a second sensor 18 different than the first sensor 18. For example, at Step: 216, a first sensor may determine first systolic and diastolic blood pressures of patient 14, and a second sensor may determine a $SpO_2$ value of patient 14. In such embodiments, it is understood that such values may be determined by the different first and second sensors 18 each time control returns to Step: 216 during the sequence of value determinations.

In exemplary embodiments, value determinations may be made at Step: 216 during inflation of cuff 12 and/or prior to cuff 12 being substantially completely inflated. For example, such value determinations may be made while vessel 10 is only partially occluded, and in such exemplary embodiments, one or more of the value determinations may be made during transition of vessel 10 of patient 14 from unoccluded to at least partially occluded. In such exemplary embodiments, such value determinations may be made in a relatively short period of time, thereby minimizing the overall time required for controller 20 to perform the value determination sequence. Depending on the number of value determinations selected by the user, in exemplary embodiments, the time required for controller 20 to perform the value determination sequence may be less than or equal to approximately two minutes, and in further exemplary embodiments, the time required may be less than or equal to approximately one minute. As described above, in exemplary embodiments in which the baseline has not been provided by the user at Step: 210, the first value determined at Step: 216 may be utilized by controller 20 as an initial baseline value.

In one embodiment, at Step: 216, controller 20 may use an algorithm stored in memory in order to determine a value indicative of a hemodynamic parameter using oscillometric pulse data obtained during inflation of cuff 12 and/or during the transition of vessel 10 from substantially unoccluded to at least partially occluded. The data may be analyzed in real time until such a point that an algorithm deems the data sufficient for a reading determination. Such data can relate to the maturity of a pulse envelope or the amount of envelope found during inflation. The collected pulse data can be filtered and/or conditioned. In other embodiments, a model curve can be fit to the data. In yet other embodiments, data can be submitted to a trained network of mathematical routines. Such analysis can be used to determine a systolic pressure or a diastolic pressure.

For example, the SureBP algorithm could be used to determine a systolic pressure. Such an algorithm is described in "Clinical evaluation of the Welch Allyn SureBP algorithm for automated blood pressure measurement," by Bruce Alpert, which is hereby incorporated by reference in its entirety. Such an algorithm can provide an accurate measure of systolic pressure during inflation, whereby the mean error is less than about 1 mmHg and the standard deviation of the mean error is less than about ±7 mmHg. In other embodiments, such an algorithm could provide a mean error of less than about 5 mmHg and a standard deviation of less than about ±5 mmHg. Such a method of blood pressure determination may comprise a suprasystolic measurement in a fast blood-pressure cycle. Such a suprasystolic blood-pressure determination may be completed in less time than a typical blood pressure assessment alone, such as, for example, about 25 seconds. The time is reduced in part because cuff re-inflation can be avoided.

Figure 4:
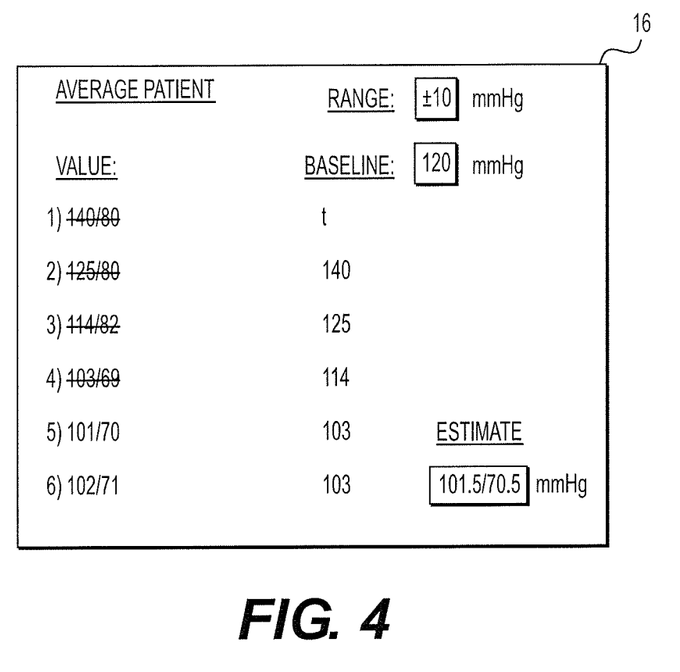
FIG. 4 illustrates a further user interface associated with the exemplary patient monitoring system of FIG. 1.

As illustrated by the display of exemplary user interface 16 shown in FIG. 4, one or more of the values determined at Step: 216 may be displayed and/or otherwise outputted by user interface 16 during and/or after Step: 216. In exemplary embodiments, such values may be displayed in list and/or table form, and one or more of the baseline value, predetermined range, and type/name of the selected value may also be displayed.

Once a value has been determined at Step: 216, control may proceed to Step: 218 where controller 20 may determine whether the determined value, for example, a first value, is within an acceptable range of a baseline, such as the baseline value selected at Step: 210. For example, at Step: 218, controller 20 may determine a difference between the value determined at Step: 216 and the baseline value selected at Step: 210. If controller 20 determines that the difference is less than or equal to the range selected at Step: 210 (Step: 218—Yes), controller 20 may identify the value as "acceptable" at Step: 220, and control may proceed to Step: 226.

If, on the other hand, controller 20 determines that the difference is greater than the range selected at Step: 210 (Step: 218—No), controller 20 may set the value determined at Step: 216, for example, the first value, as the new baseline value for future comparisons at Step: 218. In some exemplary embodiments, the baseline value selected at Step: 210 may also be deleted and/or otherwise removed from a memory of controller 20 at Step: 222. In this way, the baseline of the present disclosure may be dynamic in nature. In other words, each time controller 20 determines that the presently determined value is outside of a predetermined range of the current baseline, controller 20 may update (i.e., replace) the current baseline with the measured value. The updated baseline will then be used in future determinations at Step: 216. The replacement of consecutive baselines is illustrated in the exemplary display of user interface 16 shown in FIGS. 4 and 5. Controller 20 may then identify the value as "unacceptable" at Step: 224, and control may proceed to Step: 226. Additionally, in exemplary embodiments in which the baseline has not been selected by the user at Step: 210, controller 20 may determine that the first value determined at Step: 216 is within an acceptable range of the baseline at Step: 218 since in such embodiments the initial baseline will be set equal to the first value.

At Step: 226, controller 20 may determine whether a desired number of value determinations have been performed. For example, controller 20 may compare the number of desired value determinations selected at Step: 210 with a count value that is automatically tabulated by a counter, timer, or other like component of controller 20. Such a count value may comprise, for example, a running tally of the value determinations performed by system 100 in the present sequence of value determinations. If, at Step: 226, controller 20 determines that such a count value is less than the number of desired value determinations selected at Step: 210 (Step: 226—No), control may proceed to Step: 216, in a closed-loop manner, whereby another (for example, a second) value may be determined. If, on the other hand, controller 20 determines that such a count value is equal to the number of desired value determinations selected at Step: 210 (Step: 226—Yes), control may proceed to Step: 228 where controller 20 may determine whether any acceptable values have been determined in the present value determination sequence.

In exemplary embodiments, controller 20 may reference the identifications made at Steps: 220 and 224 in making the determination at Step: 228. For example, the identifications made at Steps: 220 and 224 may be stored in memory of controller 220 during the various value determinations described above. In such embodiments, controller 20 may reference the identifications stored in memory to make the determination at Step: 228. If none of the values determined by system 100 in the present value determination sequence qualify as "acceptable" (Step: 228—No), control may proceed to Step: 230 where controller 20 may control user interface 16 to output each of the unacceptable values. Such unacceptable values are illustrated in, for example, FIGS. 4 and 5 as being crossed-out.

In further exemplary embodiments, the values determined at Step: 216 may be output by user interface 16, in real time, after each value determination without regard to whether the value is acceptable or unacceptable. Moreover, once a new value has been set as the baseline at Step: 222, all previous values determined in the current value determination sequence may be deemed "unacceptable" by controller 20 at Step: 224. In such embodiments, controller 20 may control user interface 16 to cross-out each of the unacceptable values at Step: 224 in response to such a determination, and such crossed-out values may be output to a user by the display of user interface 16 in real time.

Figure 5:
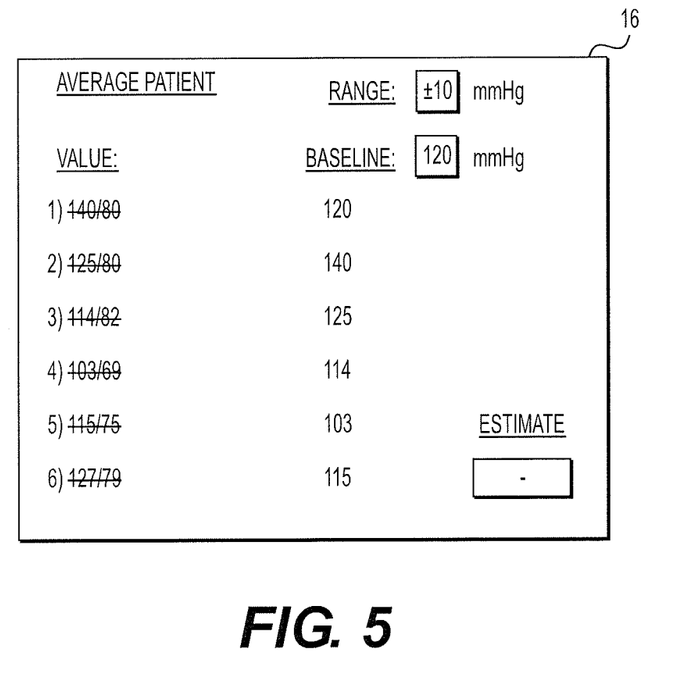
FIG. 5 illustrates yet another user interface associated with the exemplary patient monitoring system of FIG. 1.

As shown in FIG. 5, if none of the values determined by system 100 in the present value determination sequence qualify as acceptable (Step: 228—No), no estimate may be output by system 100. In further exemplary embodiments, if none of the values determined by system 100 in the present value determination sequence qualify as acceptable, controller 20 may output the last determined value as the estimate of the hemodynamic parameter. In such an exemplary embodiment, and given the exemplary determined blood pressure values 1-6 shown in FIG. 5, controller 20 would output an estimated blood pressure of 127/79 mmHg (i.e., determined value 6).

If, on the other hand, at least one of the values determined by system 100 in the present value determination sequence qualifies as "acceptable" (Step: 228—Yes), control may proceed to Step: 232 where controller 20 may determine an estimate of the hemodynamic parameter based on the acceptable values. In exemplary embodiments in which the user identified at least one value determination for omission during Step: 210, the one or more values corresponding to the selected value determinations may not be used by controller 20 in determining the estimate at Step: 232. Control may then proceed from Step: 232 to Step: 234 where controller 20 may control user interface 16 to output the estimate. Such an estimate is illustrated by the display of exemplary user interface 16 shown in FIG. 4. In exemplary embodiments in which the estimated hemodynamic parameter comprises an average blood pressure of the patient, the estimate may be displayed as an average systolic blood pressure over an average diastolic blood pressure as shown in FIG. 4.

The exemplary systems and methods of the present disclosure overcome various deficiencies of known prior art devices. For example, system 100 is configured to estimate a desired hemodynamic parameter in less time than known systems, thereby reducing the overall evaluation time required for each patient. Additionally, since system 100 is configured to utilize a dynamic baseline while determining values indicative of the desired hemodynamic parameter, system 100 may only utilize a subset of stabilized determined values in determining the estimate of the hemodynamic parameter. Due to this configuration, the estimate is typically more accurate than estimates produced by other known systems.

Other embodiments of the present disclosure will be apparent to those skilled in the art from consideration of the specification and practice of the disclosure contained herein. It is intended that the specification and examples be considered as exemplary only, with a true scope and spirit of the present disclosure being indicated by the following claims.

What is claimed is:

1. A method of determining a value indicative of a hemodynamic parameter of a patient, comprising:
    performing a plurality of value determinations, wherein performing the plurality of value determinations includes
        inflating an inflatable cuff disposed around a limb of the patient until a vessel within the limb is at least partially occluded,
        determining, with a sensor, a first value indicative of the hemodynamic parameter, wherein the first value is an initial determined value and comprises one of a cuff pressure, cuff volume, or blood pressure value,
        determining, with a controller in communication with the sensor, a difference between the first value and a baseline associated with the first value,
        replacing the baseline with the first value, in a memory of the controller, if the difference is outside of a predetermined range;
    determining, with the controller, an estimate of the hemodynamic parameter based on values determined during the plurality of value determinations; and outputting the estimate.

2. The method of claim 1, wherein the first value comprises a systolic blood pressure of the patient and a diastolic blood pressure of the patient, and wherein determining the estimate comprises calculating an average systolic blood pressure of the patient over an average diastolic blood pressure of the patient.

3. The method of claim 1, further including receiving an input indicative of the predetermined range.

4. The method of claim 1, further including determining that fewer than a desired number of value determinations have been performed, and automatically determining at least one additional value indicative of the hemodynamic parameter in response to the determination that fewer than the desired number of value determinations have been performed.

5. The method of claim 1, further including determining that a desired number of value determinations have been performed, and automatically determining whether any acceptable values have been determined in response to the determination that the desired number of value determinations have been performed, wherein the acceptable values comprise a subset of values determined during the plurality of value determinations and are identified as being acceptable at least partly as a result of a difference between each respective value of the subset of values and the baseline being within the predetermined range.

6. The method of claim 5, wherein performing the plurality of value determinations includes determining a plurality of values indicative of the hemodynamic parameter, the method further including outputting at least one value of the plurality of values in response to determining that no acceptable values have been determined.

7. The method of claim 5, wherein performing the plurality of value determinations includes determining a plurality of values indicative of the hemodynamic parameter, the method further including determining that acceptable values have been determined, and determining the estimate based on only the acceptable values.

8. The method of claim 1, further including receiving an input indicative of a time interval between initiation of each value determination of the plurality of value determinations.

9. The method of clam 1, further including receiving an input indicative of a desired number of value determinations to be performed, and performing the plurality of value determinations based on the desired number.

10. The method of claim 1, further including receiving an input comprising a value determination selection, wherein, in response to the selection, a value corresponding to the selected value determination is omitted from the determination of the estimate.

11. The method of claim 10, wherein the input is received prior to performing the plurality of value determinations.

12. The method of claim 1, wherein the plurality of value determinations is performed in less than approximately one minute.

13. The method of claim 1, wherein:
the sensor comprises a blood pressure sensor configured to generate a signal associated with the vessel of the patient, and
determining the first value comprises determining a systolic blood pressure of the patient during transition of the vessel of the patient from unoccluded to at least partially occluded.

14. The method of claim 1, further including
receiving a first input indicative of a wait time,
receiving a second input comprising a value determination initiation command, and
delaying determining the first value by the wait time.

15. The method of claim 1, wherein the sensor comprises a first sensor, the method further comprising determining a second value indicative of an additional hemodynamic parameter with a second sensor different than the first sensor.

16. The method of claim 1, wherein the first value comprises a systolic blood pressure of the patient.

17. The method of claim 1, further including:
determining, with the sensor, a second value indicative of the hemodynamic parameter, wherein the second value comprises a value determined immediately subsequent to the first value and comprises one of a cuff pressure, cuff volume, or blood pressure value;
determining, with the controller, a difference between the second value and the baseline;
replacing the baseline with the second value, in the memory of the controller, if the difference is outside of the predetermined range; and
determining, with the controller, the estimate of the hemodynamic parameter based at least partly on the second value.

18. A method of determining a value indicative of a blood pressure of a patient, comprising:
automatically performing a plurality of value determinations, in a closed-loop manner, in response to receiving at least one input associated with the plurality of values, wherein performing the plurality of value determinations includes
inflating a cuff disposed around a limb of the patient until a vessel within the limb is at least partially occluded,
determining a first blood pressure value of the patient while the cuff is being inflated,
determining whether a component of the first blood pressure is within a predetermined range of a baseline blood pressure value,
substantially deflating the cuff and reinflating the cuff until the vessel is at least partially occluded,
determining a second blood pressure value of the patient while the cuff is being reinflated, and
determining, if the first blood pressure value is within the predetermined range of the baseline, whether the second blood pressure value is within the predetermined range of the baseline, and
if the first blood pressure is outside of the predetermined range of the baseline, determining whether the second blood pressure is within the predetermined range of the first blood pressure value;
replacing the baseline with the first blood pressure value, in a memory of a controller, in response to determining that the first blood pressure value is outside of the predetermined range of the baseline, wherein the first blood pressure value is an initial determined value, and wherein the second blood pressure value is a value determined immediately subsequent to the first value;
determining an estimate of the blood pressure of the patient, wherein the estimate is based on at least one of the first and second blood pressure values; and outputting the estimate.

19. The method of claim 18, wherein determining the estimate comprises calculating an average systolic blood pressure of the patient, and wherein the average is calculated using the first blood pressure value only if the first blood pressure value is within the predetermined range of the baseline.

20. The method of claim 18, wherein the at least one input is indicative of the predetermined range.

21. The method of claim 18, wherein the at least one input comprises a first input indicative of a time interval between initiation of each value determination of the plurality of value determinations, and a second input indicative of a wait time, the method further including delaying determining the first blood pressure value by the wait time.

22. The method of claim 18, wherein the at least one input comprises a value determination selection, the method further including omitting a blood pressure value corresponding to the selected value determination from the determination of the estimate.

23. The method of claim 18, wherein the at least one input is indicative of a desired number of value determinations to be performed, the method further including performing the plurality of value determinations based on the desired number.

24. A patient monitoring system, comprising:
a sensor configured to determine a value indicative of a hemodynamic parameter of a patient during transition of a vessel of the patient from unoccluded to at least partially occluded;
an inflatable cuff configured to be disposed around a limb of the patient, wherein inflation of the cuff transitions the vessel from unoccluded to at least partially occluded; and a controller in communication with the sensor, the controller including a memory and being configured to assist in performing a plurality of value determinations, wherein performing the plurality of value determinations includes:
- determining, with the sensor, a first value indicative of the hemodynamic parameter, wherein the first value is an initial determined value and comprises one of a cuff pressure, cuff volume, or blood pressure value,
- determining, with the controller, a difference between the first value and a baseline associated with the first value, and
- replacing the baseline with the first value, in the memory of the controller, if the difference is outside of a predetermined range,
  - wherein the controller is further configured to determine an estimate of the hemodynamic parameter based on values determined during the plurality of value determinations, and to output the estimate.

25. The system of claim 24, further including a user interface in communication with the controller and configured to receive an input from a user, the input being associated with performing the plurality of value determinations.

26. The system of claim 25, wherein the input comprises a first input indicative of the baseline and a second input indicative of the range.

27. The system of claim 25, wherein the input comprises a first input indicative of a time interval between initiation of each value determination of the plurality of value determinations, and a second input indicative of a wait time, the controller being configured to delay determining the first value by the wait time.

28. The system of claim 25, wherein the input comprises a value determination selection, the controller being configured to omit a value corresponding to the selected value determination when determining the estimate.

29. The system of claim 25, wherein the input is indicative of a desired number of value determinations to be performed, the controller being configured to perform the plurality of value determinations based on the desired number.

* * * * *